United States Patent
O'Connor et al.

(10) Patent No.: US 7,897,057 B1
(45) Date of Patent: Mar. 1, 2011

(54) SENSOR FOR DETECTION OF GAS SUCH AS HYDROGEN AND METHOD OF FABRICATION

(75) Inventors: Paul B. O'Connor, San Pedro, CA (US); Kisholoy Goswam, Lomita, CA (US)

(73) Assignee: Optech Ventures, LLC, Torrance, CA (US)

(*) Notice: Subject to any disclaimer, the term of this patent is extended or adjusted under 35 U.S.C. 154(b) by 680 days.

(21) Appl. No.: 11/680,546

(22) Filed: Feb. 28, 2007

Related U.S. Application Data

(62) Division of application No. 09/946,871, filed on Sep. 4, 2001, now abandoned.

(51) Int. Cl.
*C03C 15/00* (2006.01)

(52) U.S. Cl. .............. 216/24; 216/56; 216/83

(58) Field of Classification Search .......... 216/57
See application file for complete search history.

(56) References Cited

U.S. PATENT DOCUMENTS

| | | | | |
|---|---|---|---|---|
| 4,318,770 A * | 3/1982 | Chakupurakal | ............ | 216/90 |
| 4,453,151 A * | 6/1984 | Leary et al. | ............ | 338/34 |
| 4,872,759 A * | 10/1989 | Stich-Baumeister et al. | | 356/432 |
| 5,063,164 A * | 11/1991 | Goldstein | ............ | 436/169 |
| 5,107,316 A * | 4/1992 | Jelley et al. | ............ | 257/432 |
| 5,268,972 A * | 12/1993 | Tabacco et al. | ............ | 385/12 |
| 5,290,103 A * | 3/1994 | Fevrier et al. | ............ | 374/131 |
| 5,346,671 A * | 9/1994 | Goswami et al. | ............ | 422/86 |
| 5,405,583 A * | 4/1995 | Goswami et al. | ............ | 422/86 |
| 5,618,493 A * | 4/1997 | Goldstein et al. | ............ | 422/57 |
| 5,835,229 A * | 11/1998 | Daniels | ............ | 356/435 |
| 6,006,582 A * | 12/1999 | Bhandari et al. | ............ | 73/23.2 |
| 6,391,808 B1 * | 5/2002 | Stiegman | ............ | 501/12 |
| 6,535,658 B1 * | 3/2003 | Mendoza et al. | ............ | 385/12 |
| 6,730,270 B1 * | 5/2004 | O'Connor | ............ | 422/98 |
| 7,306,951 B1 * | 12/2007 | Benson et al. | ............ | 436/144 |

OTHER PUBLICATIONS

S. Sekimoto et al., A fiber-optic evanescent-wave hydrogen gas sensor using palladium-supported tungsten oxide, Sensors and Actuators B 66 (2000) 142-145, no month available.

X. Bevenot et al., Hydrogen leak detector using optical fibre sensor for aerospace applicatons, Sensors and Actuators B 67 (2000) 57-67, no month available.

\* cited by examiner

*Primary Examiner* — Anita K Alanko
(74) *Attorney, Agent, or Firm* — Lawrence S. Cohen

(57) ABSTRACT

A gas sensor system and its method of fabrication is disclosed. The sensor system comprises an optrode, light source, and a light detector. In a sensor for hydrogen gas, the optrode is comprised of a porous substrate into which an intimate mixture of reagent and catalyst is incorporated. The mixture reacts with the hydrogen to produce a color/intensity change in relation to the concentration of gas. The optrode further includes a reversing agent, boron, to restore the benchmark conditions of the sensor system in real-time. The method of fabricating the optrode includes the steps of cleaning; etching to achieve the proper porosity; incorporating the reagent, catalyst, and reversing agent using capillary action; and removing excess reagent and catalyst.

2 Claims, 6 Drawing Sheets

SENSOR FOR DETECTION OF GAS SUCH AS HYDROGEN AND METHOD OF FABRICATION

RELATED APPLICATIONS

The present application is a divisional application of U.S. application Ser. No. 09/946,871 filed on Sep. 4, 2001, now abandoned.

FIELD OF THE INVENTION

The present invention relates to a gas sensor and the method of fabricating the same. More particularly, the invention relates to a hydrogen sensing apparatus comprised of a substrate into which a reagent is uniformly incorporated, the reagent having optical properties that change in the presence of the gas to be sensed.

BACKGROUND OF THE INVENTION

Hydrogen gas is prevalent in many commercial and industrial settings. There is currently a need for a small, rugged, inexpensive hydrogen sensor for applications where hydrogen is used, produced, or may potentially harm equipment or processes. Hydrogen sensor applications include lead-acid battery storage and charging stations, furnaces, electric power plants, petroleum processing plants, submarines, hydrogen-fueled vehicles, and radioactive waste tanks.

There are prior art hydrogen sensors, including thin-film sensors fabricated from optical fibers. Such prior art discloses thin-film, hydrogen sensing systems such as the ones represented by the sensing element 100 illustrated in FIG. 1A and the sensing element 110 illustrated in FIG. 1C. Referring to FIG. 1A and the corresponding cross section in FIG. 1B, we see that the fiber sensing element 100 is comprised of a silica core 101 with the outer cladding removed, a first layer 102 of transparent silicone resin circumferentially deposited about the core 101, and a second layer 103 of silicone resin dispersed with a palladium-supported tungsten oxide powder.

Referring to FIG. 1C and the corresponding cross section in FIG. 1D, we see that the second sensing element 110 is comprised of a silica core 111 of an optical fiber with the outer cladding removed and a layer 112 formed using a sol-gel technique. More specifically, the layer 112 includes tungsten and palladium impregnated into the silica core by dip-coating the optical fiber in an aqueous solution of sodium tungstate. The sensing element 110 is subsequently calcined at 500 degrees Celsius for three hours.

The presence of hydrogen is determined with the sensing elements 100, 110 by analyzing the reflectance spectra at the upper end of the visible spectrum or the transmission spectra at one or more wavelengths between 530 and 800 nanometers.

In comparison to the present invention, each of these prior art sensing elements is relatively insensitive to hydrogen gas because the reactive component, the tungsten and palladium mixture, is confined to the relatively thin and discrete layers 103, 112 at the outermost portion of the optical fiber. Furthermore, the prior art sensing elements 100, 110 exhibit long recover times and limited sensitivity to relatively high concentrations of hydrogen.

BRIEF SUMMARY OF THE INVENTION

The invention relates to a sensor system configured to measure the concentration of a gas such as hydrogen. The sensor system is comprised of an optrode, a light source for generating visible or ultraviolet light used to interrogate the optrode, and a light detector to measure optical changes in the optrode. Light from the light source is launched into the optrode, which reacts with the hydrogen to produce a color change, and is reflected or transmitted into the light detector. The color change, specifically a change in intensity at one or more wavelengths that occurs as a result of the presence of gas, may be measured at the light detector. A signal processing unit may also be employed to quantitatively evaluate spectral changes in the optrode output.

In some embodiments, the optrode is comprised of a porous substrate into which an indicator material is incorporated. The substrate is preferably glass, which may be created through a sol-gel process, for example, or selected from a variety of porous and non-porous materials available commercially and described below. The porous substrate includes an extensive network of interconnected pores, creating a very large surface area comparable to that of a substrate having pores with a mean diameter greater than seven nanometers. The substrate is also inert with respect to hydrogen and optically transparent to light used to interrogate the optrode.

The indicator material is incorporated into the pores of the substrate and indicates the presence of gas by changing in an optically detectable manner, the change effectively altering the intensity or spectral character of the interrogating light signal, for example. The indicator material in the first embodiment is comprised of an intimate mixture of reagent, catalyst, molecular barrier, and reversing agent. The reagent can be a tungsten ion or one or more of a number of suitable alternative substances that give rise to a change in color or intensity or both in the presence of hydrogen. The optrode may also include palladium or other suitable catalyst to promote the reaction of reagent with the gas to be sensed. The molecular barrier, such as calcium bromide, inhibits the diffusion of hydrogen into the substrate. The reversing agent, such as boron, oxidizes the reagent and restores the benchmark conditions of the sensor system in real-time.

The method of fabricating the optrode includes the steps of providing a substrate, which entails either the selection or preparation of the substrate; cleaning the substrate to remove contaminates; etching the substrate to achieve a pore diameter sufficient to attain a relatively large sensing surfacing; incorporating indicator solution into the substrate, the solution comprising various solutes including reagent, catalyst, molecular barrier, and reversing agent; and removing excess indicator material.

Etching creates or enlarges pores in the substrate, promotes the inter-connectivity between pores, and reduces the solid mass separating pores. This in turn promotes the diffusion of gas and penetration of indicator material into the interior of the substrate where they may react. Etching also retards the unwanted diffusion of materials into the solid glass, which would adversely affect the sensor performance. The result is a compact three-dimensional sensing device with a relatively large sensing surface.

The indicator solution includes non-organic water-soluble materials that are incorporated into the substrate in a "wet chemistry" process to insure intimate contact between the reagent and catalyst, thereby requiring a minimum quantity of catalyst to produce the desired reaction. The incorporation of the indicator material utilizes capillary action, i.e. "wicking," to uniformly permeate and distribute indicator material throughout the substrate.

A molecular barrier is incorporated into the substrate, preferably concurrently with the indicator material, to minimize unwanted diffusion of hydrogen into the glass. A reversing agent is also incorporated into the substrate, preferably with the indicator material, to stimulate reversal of the chemical reaction that gave rise to the optically detectable change.

In the final step of fabrication, the optrode is treated to remove excess indicator material that is loosely bound to the substrate, thereby reducing noise and drift in the sensor system.

The sensing system of the present invention provides improved sensitivity, increased immunity to contaminants, and reduced manufacturing costs compared to prior art devices.

DETAILED DESCRIPTION OF THE INVENTION

Figures 1A, 1B:
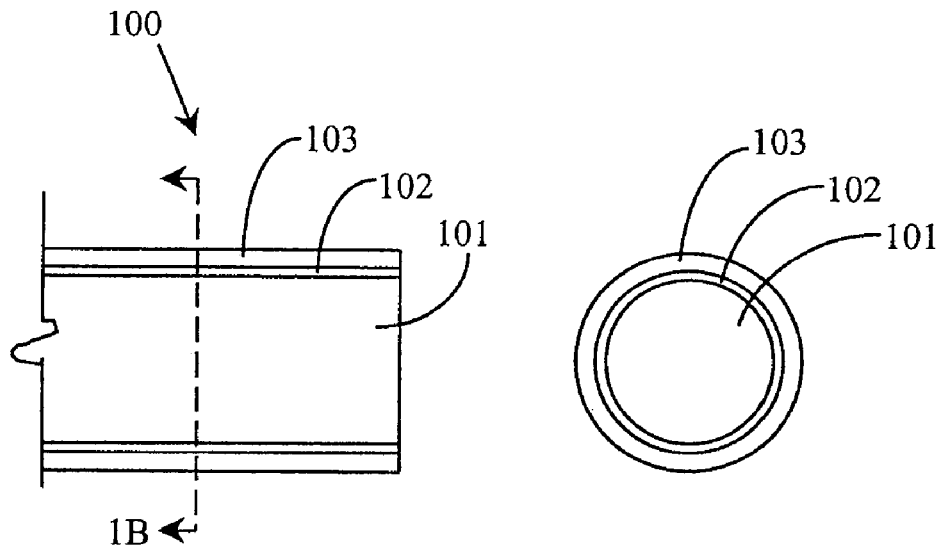
FIGS. 1A-B is a schematic representation of a sensing element of a hydrogen sensor system according to the prior art.
Figures 1C, 1D:
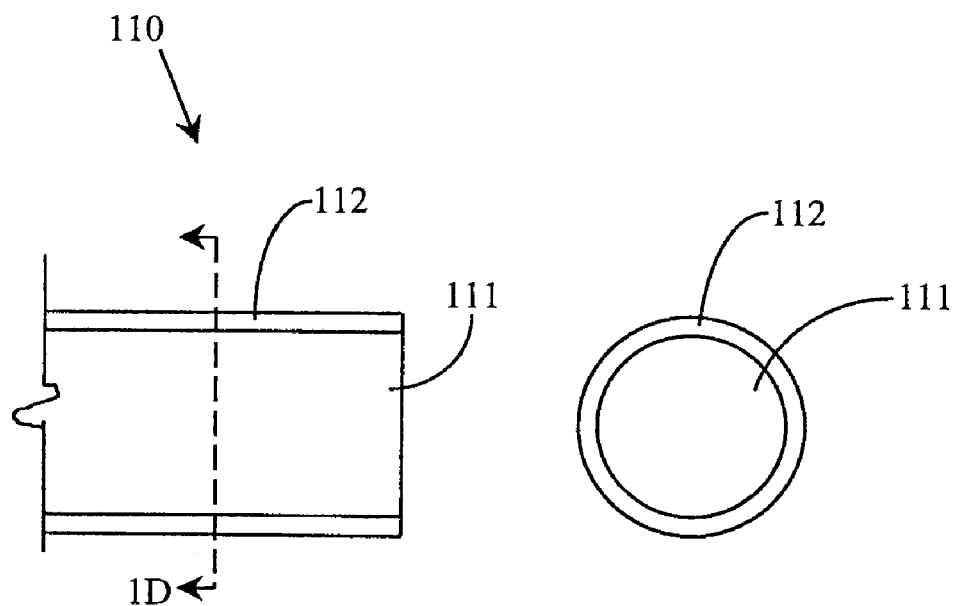
FIGS. 1C-D is a schematic representation of a sensing element in hydrogen sensor system according to the prior art.
Figure 2:
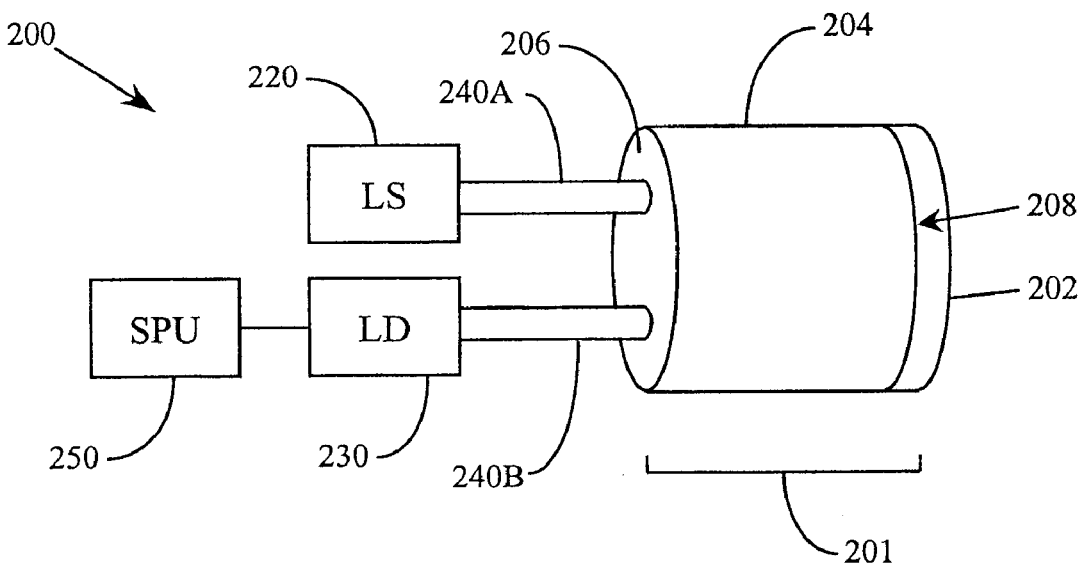
FIG. 2 is a schematic representation of the gas sensor system according to the first embodiment of the present invention.

Referring to FIG. 2, we see a gas sensor system according to the first embodiment of the present invention. The gas sensor system 200 includes a gas sensor 201 with an optional mirror 202, light source 220, light detector 230, coupling means 240A and 240B, and signal processing unit 250. In this and other embodiments, the gas sensor 201 receives an input signal generated by the light source 220 and generates an output signal by reacting with the gas. The output signal is then reflected or conveyed to the light detector 230 and subsequently analyzed by the signal processing unit 250 to determine the concentration of gas (not shown) to be sensed. The sensor 201 is designed to detect hydrogen, although the system 200 and its method of fabrication may be adapted to detect one or more different gases.

The light source 220 generates an input signal illustratively in the visible or ultraviolet light spectrum. The input signal is used to interrogate the sensor 201 and observe chemical and or physical changes in the presence of the gas to be sensed. The proper input signal will depend on the gas to be sensed, the chemical composition of the gas sensor 201, and the mechanism giving rise to the optically detectable change.

The light source 220 is preferably selected to provide light at a bandwidth coinciding with the absorption peak of the gas sensor 201. In the preferred embodiment, the light source 220 is a light emitting diode (LED) that generates light within a narrow bandwidth, the peak emission corresponding to a wavelength at approximately 470 nanometers in the case of hydrogen gas. The input signal generated by the light source 220 is conveyed to the sensor 201 using a light coupling means 240 such as an optical fiber 240A or comparable form of wave-guide. The concentration of hydrogen may then be correlated with the change in intensity in blue light, for example, recovered from the sensor 201.

One skilled in the art will recognize that a light source 220 emitting at a bandwidth coinciding with the absorption peak of the sensor 201 in the absence of gas may also be used. As the sensor 201 is exposed to gas, its absorption peak shifts away from the wavelength of the input signal, causing the intensity of light from the sensor 201 to increase.

The sensor 201 is comprised of an optrode 204 and an optional mirror 202. In this embodiment, the optrode 204 may be a cylindrically-shaped silica glass rod. One skilled in the art will appreciate that numerous alternative configurations may be used including rectangular, square, disk, pipe, optical fiber, slab, prism, strip, cube, film and planar optrodes.

The proximal end 206 of the optrode 204 is brought into optical communication with the light detector 230 using coupling means 240B, which is preferably an optical fiber or similar wave-guide. The light that is collected by the optical fiber 240B constitutes the output signal, which is conveyed to the light detector 230. The detector 230 in this embodiment is a photo-multiplier tube (PMT), although a PIN diode or spectrophotometer with discrete wavelength resolution would be equally suitable. Note that the mirror 202 may be used to increase the recovery of light from the sensor 201 by reflecting light impinging on the distal end 208 of the optrode 204.

The Optrode

The optrode 204 is comprised of a homogeneous composition of indicator material and its host material, the substrate. The indicator material includes the reactive component of the optrode 204 and manifests an optically detectable change when exposed to the gas to be sensed. In the present embodiment, the indicator material is applied to the surface of the substrate which supports the indicator material and transmits light used to interrogate the indicator material.

A proper substrate possesses a large surface area relative to its volume. The surface area includes both the external surface of the substrate as well as internal surfaces attributable to the microstructure of the substrate. Materials having large "pores" are particularly well suited because their structure defines a very large area "wall" or detection surface onto which the indicator material may be deposited. The pores may occur as a natural byproduct of the manufacturing process, or may be artificially created or enlarged during the sensor production.

In the preferred embodiment, silica glass was selected as the porous substrate. These pores arise from the manufacturing processes and involve a phase separation reaction in which one material is leached out from another, for example.

The pores in silica glass are randomly distributed throughout the body of the glass and are generally interconnected. The pores are of different sizes but may be characterized by a mean diameter and surface area. Commercially available porous glass typically has a mean pore diameter in the range of four to seven nanometers and an effective surface area of approximately 200 square meters per gram. In the present invention, the mean pore diameter is greater than seven nanometers, preferably on the order of 20 nanometers.

The pores of the substrate may be augmented to increase their surface area and ultimately the sensitivity of the sensor system 200. In particular, the pores can be enlarged by etching the substrate in the manner described below. Etching provides access to the pores at the interior of the substrate, thus increasing the detection surface of the optrode 204 as well as the diffusion of hydrogen through the optrode 204.

One skilled in the art will recognize that there are numerous alternative substrate materials from which to choose. Suitable types of glass include quartz, Pyrex®, Vycor® glass (PVG), sodalime, phosphate, borosilicate, fluoride, chalcogenide, and fluorozirconate. Other suitable substrate materials include organic rods and organic/inorganic films.

A substrate can also be formed using gel-forming materials such as sol-gel, silica gel, hydrogel, aerogel, or xerogel. Suitable non-porous matrices can be formed using film-forming cross-linkable/polymerizable monomers and polymers, including poly vinyl chloride (PVC), carboxylated PVC, polystyrene, cellulose derivatives, and variations of plexiglass, silanes, siloxanes, and silicones. Polymers and organic materials can be pure or doped, including plexiglass and polyimide.

In addition, a substrate can also be formed from amorphous and single-crystal or polycrystalline materials, inorganic and organic compounds, liquids, liquid crystals, and semiconductor materials. Single crystal materials include, for example, silicon, lithium niobate, lithium tantalite, barium tellurate, and garnets. The substrate may also be formed from integrated optic materials including oxides, nitrides, sulfides, oxynitrides, zirconates, and titanates.

Detection of the gas to be sensed is reliant on the presence of the indicator material. The indicator material in the present invention is incorporated into the substrate in one of various processes described below. In some embodiments, the indicator layer is deposited on the walls of the pore throughout the substrate. In other embodiments, the indicator material is a component of the matrix of the substrate produced by a sol-gel process. In either case, the indicator material is distributed through the substrate in a substantially uniform or homogeneous manner. The concentration of indicator material must be in an amount effective to induce a detectable change in color or intensity alternatively or additively in the presence of the gas to be sensed. The precise concentration is also subject to variation depending on the desired sensitivity and dynamic range of the sensor system 200.

The gas to be sensed diffuses into the optrode 204 through the network of pores where it reacts or interacts with the indicator material, resulting in a chemical or physical change in the indicator material. The preferred form of indicator material for a hydrogen sensor is comprised of a reagent in the form of tungsten complex and a catalyst such as palladium ion. In the case of a hydrogen sensor in which the indicator material includes tungsten, the change is in the form a shift of the absorption peak from a yellow wavelength range to a blue wavelength range. In the absence of hydrogen, tungsten and palladium persist in a stable state in the optrode 204. In the presence of hydrogen, palladium complex ($Pd^{+2}$) is reduced, which in turn causes a partial redox reaction of the tungsten complex ($W^{+6}$). More specifically, the palladium is reduced to a neutral state by the hydrogen, such that $Pd^{+2}+H_2 \square Pd^0$, which in turn causes the tungsten to be reduced, $Pd^0+2W^+6 \square 2W^{+5}+Pd^{+2}$. It is the reduced tungsten ($W^{+5}$) that gives rise to the blue color indicating the presence and concentration of hydrogen. The concentration of gas being sensed is then indirectly observed by measuring relative changes in the light reflected or transmitted through the optrode 204.

The tungsten and palladium of a hydrogen sensor may be incorporated into the substrate together using a "wet chemical" process described below or in separate steps to form discrete layers of tungsten and palladium. The concentration of palladium is approximately one to ten percent, and preferably one to two percent, of that of tungsten where the cleaning step as described below is employed. Without the cleaning step the relative concentration of palladium must be increased to achieve a comparable change in color or intensity. Although the thickness of indicator material may vary significantly depending on the sensor application, the resulting layer or coating of tungsten and palladium is preferably an intimate mixture approximately two atoms thick. The optrode 204 of the present invention possesses a layer of tungsten and palladium having an effective sensing surface area of approximately 12 square meters, yielding high sensitivity from a relatively small volume.

One skilled in the art will recognize that there are numerous other alternative reagents that are suitable for detecting hydrogen, including molybdenum and vanadium complexes. It is recognized that these reagents may require appropriate modification of the interrogating wavelength or the light detector 230 depending on the absorption and transmission characteristics of the indicator material.

Similarly, catalysts other than palladium can be used without loss of generality. Catalysts having a neutral molecule or an ionic species with multiple oxidation states, including sources of $Pd^{+2}$, $Ru^{+3}$, or $Os^{+8}$ ions, for example, are suitable. Alternative catalysts include platinum and nickel.

The various mixtures of reagent and catalyst may exhibit any one of a number of chemical and/or physical changes that are susceptible to optical detection. These changes may include, for example, intensity changes in the absorption or emission band, color shifts or shifts in the absorption or emission band, emergence of new peak(s) or a shoulder along with the main peak(s) in the indicator spectrum and changes in the temporal or kinetic characteristics of the absorption or emission bands. The optical changes in the reagents listed above are understood to be the manifestation of reactions or interactions, either directly or indirectly through a catalyst, including redox reaction, exiplex formation, excimer formation, ion-pairing, Van der Waals interaction, dipole-dipole or coulombic interaction, and an energy transfer interaction.

The illustrative optrode 204 of this and subsequent embodiments preferably further include a "molecular barrier" to inhibit the diffusion of gas to be sensed. More specifically, the molecular barrier permits hydrogen to diffuse into the pores of the substrate but not to penetrate the solid matrix of the substrate. In the present embodiment, the molecular barrier includes calcium bromide ($CaBr_2$) which acts an "attraction site" to hydrogen and prevents hydrogen from penetrating through the layer of indicator material into the substrate where it may be trapped. The calcium bromide is preferably incorporated into the intimate tungsten and palladium mixture deposited in the pores of the substrate. Without the molecular barrier, hydrogen may be trapped in the matrix of the substrate where it would require a relatively long time to diffuse out, thus lowering the response and recovery times of the sensor system 200.

The molecular barrier may also be formed from materials that retain hydrogen molecules through induced-dipole or other types of interactions. Alternative molecular barrier species include sodium, potassium, calcium, ammonium, lithium, beryllium, magnesium, aluminum, platinum, cobalt salts with counterions including nitrates, acetates, chloride, sulfates, phosphates, chlorates, perchlorates, nitrites, carbonates, and bicarbonates.

In some embodiments of this invention, the substrate further includes a "reversing agent" incorporated into either the substrate matrix or the layer of indicator material. The purpose of the reversing agent is to return the sensor to the baseline condition by reversing the reaction that gave rise to the optically detectable change. In general, a reversing agent is an electron deficient substance such as boron, which facilitates the conversion of $W^{+5}$ to $W^{+6}$. The concentration of boron should be greater than one percent of the concentration of palladium, but not so high that is competes with tungsten in the reaction with palladium.

According to the first embodiment of the sensor system 200 used for sensing hydrogen, blue light used to interrogate the sensor 201 is reflected or reradiated toward the proximal end 206 of the optrode 204 and collected by the coupling means 240B. The collected light is conveyed to the light detector 230 where the power or intensity is determined. In other embodiments, the light detector 230 measures the aggregate power output across the entire output bandwidth. The light detector 230 may further include a diffraction grating in order to resolve and measure power at individual wavelengths. The sensor system 200 may optionally include a signal processing unit 250 to make quantitative comparisons between the light output signal from the sensor 201 and the input signal from the light source 220, for example.

The recovery of light from the sensor 201 by the coupling means 240B may be enhanced using an optical mirror 202. In general, the mirror 202 should redirect light that impinges on the distal end 208 of the sensor 201 and redirect it towards or focus on the coupling means 240B. A planar mirror may suffice although concave, convex, or complex shapes may alternatively be employed depending on the position of the coupling means 240B as well as the configuration of the optrode 204. If used, the mirror 202 should avoid interfering with or otherwise altering the spectral character of the input or output signals unless specifically accounted for in the detection process.

Figure 3:
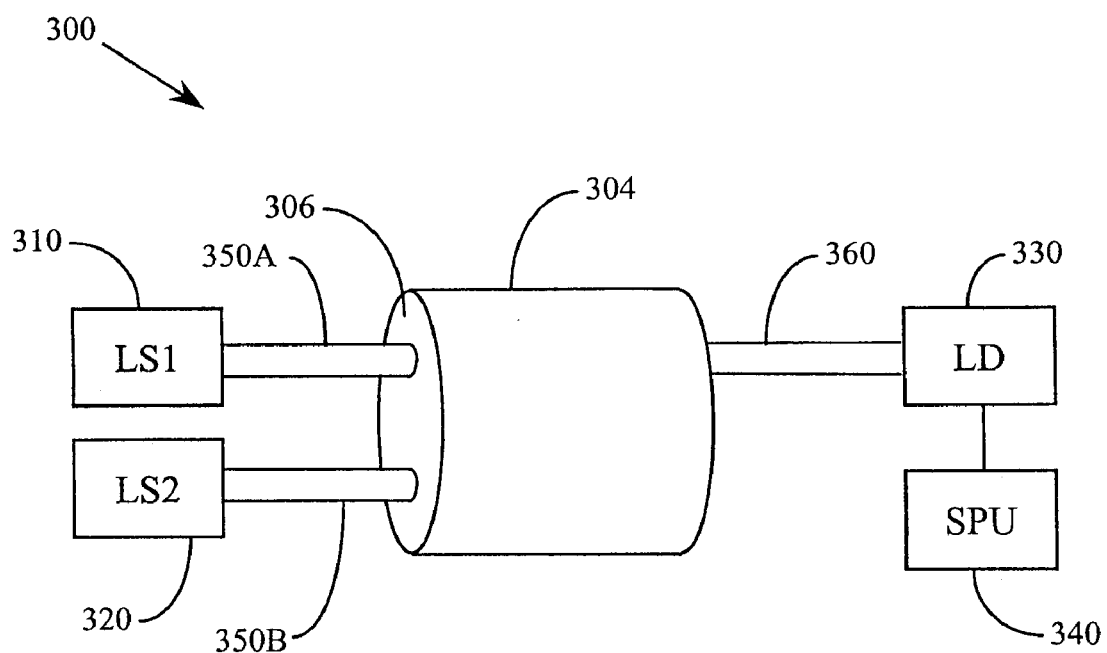
FIG. 3 is a schematic representation of the gas sensor system according to the second embodiment of the present invention.

Illustrated in FIG. 3 is a gas sensor system 300 according to the second embodiment of the present invention. The first light source, LS1, 310 generates a visible light signal that is conveyed by the first coupling means 350A to the optrode 304. The concentration of gas to be sensed is related to the intensity of the light transmitted through the optrode 304 and collected by the second coupling means 360. The power of the output signal is detected by light detector 330 and analyzed by the signal processing unit 340 in the manner described above. The sensor system may further include a second light source, LS2, 320 for generating a second light signal at a wavelength or over a bandwidth different than that of the first light source 310. This second light signal, conveyed to the proximal end 306 of the optrode 304 by coupling means 350B, may then be used as a benchmark useful for making absolute measurements of the transmission characteristics of light through the optrode 304.

Figure 4:
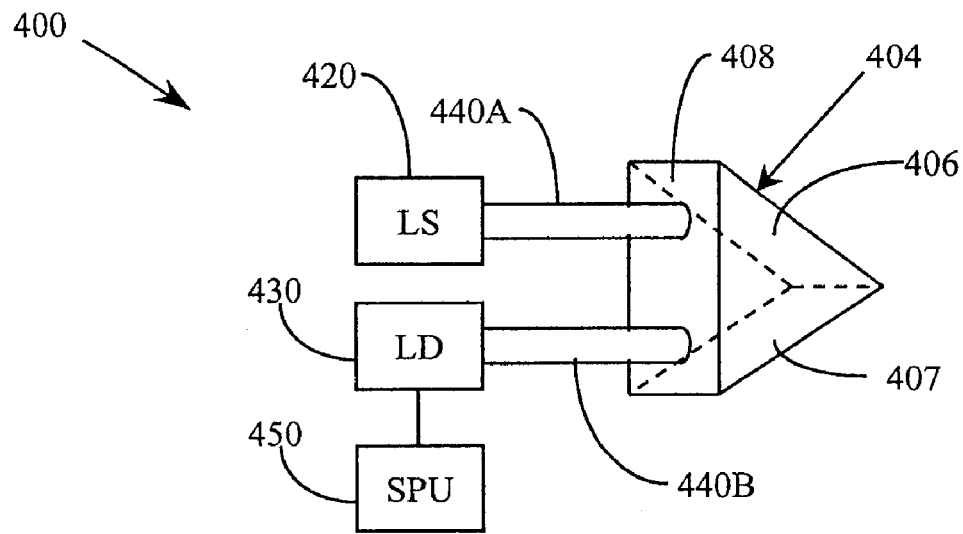
FIG. 4 is a schematic representation of the gas sensor system according to the second embodiment of the present invention.

Referring to FIG. 4, we see a gas sensor system 400 according to a third embodiment of the present invention. The light source 420, light detector 430, and signal processing unit 450 operate in a manner entirely analogous to that of the first embodiment. The primary difference is the configuration of the optrode 404, which relies on the angled orientation of the upper and lower faces 406, 407 to internally reflect and redirect the interrogating light signal from the first coupling means 440A to the second coupling means 440B. This configuration may obviate the need for the mirror 202 used in the first embodiment.

Figure 5:
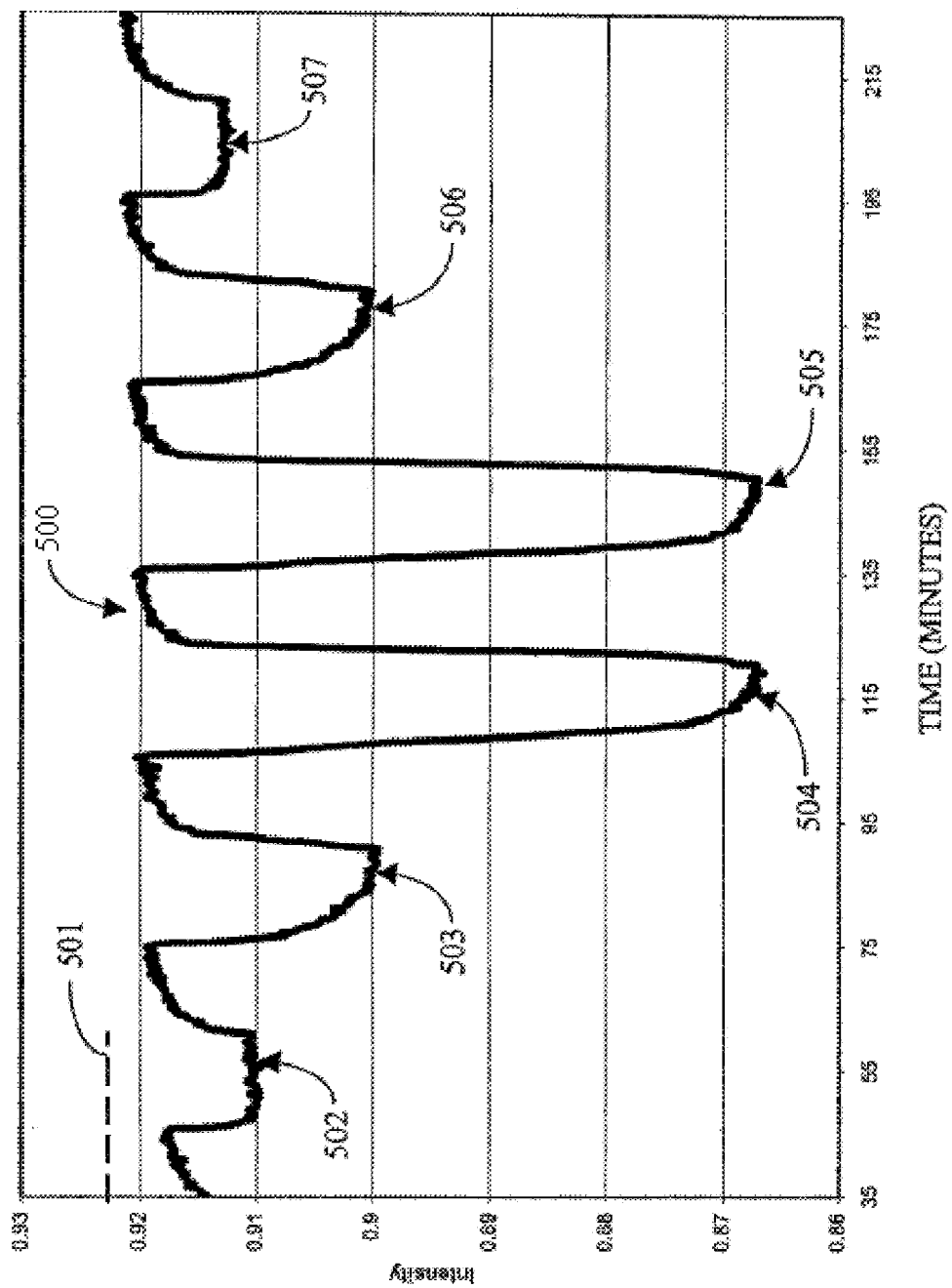
FIG. 5 is a plot of the sensor system response to variable concentrations of hydrogen.

Illustrated in FIG. 5 is a plot of the response of the sensing system of the present invention. The response curve 500 of the sensing system 200 (of FIG. 2) is plotted as a function of time for variable concentrations of hydrogen. Illustrated is a baseline 501 presenting the intensity of the optrode output signal measured with the sensor 201 exposed to zero percent hydrogen. The first and sixth peaks 502, 507 represent the output signal in one percent hydrogen, the second and fifth peaks 503, 506 corresponding to three percent hydrogen, and the third and fourth peaks 504, 505 corresponding to five percent hydrogen. As can be seen, the sensor system 200 is substantially linear and exhibits fast detection and recovery times.

Process of Manufacturing

Figure 6:
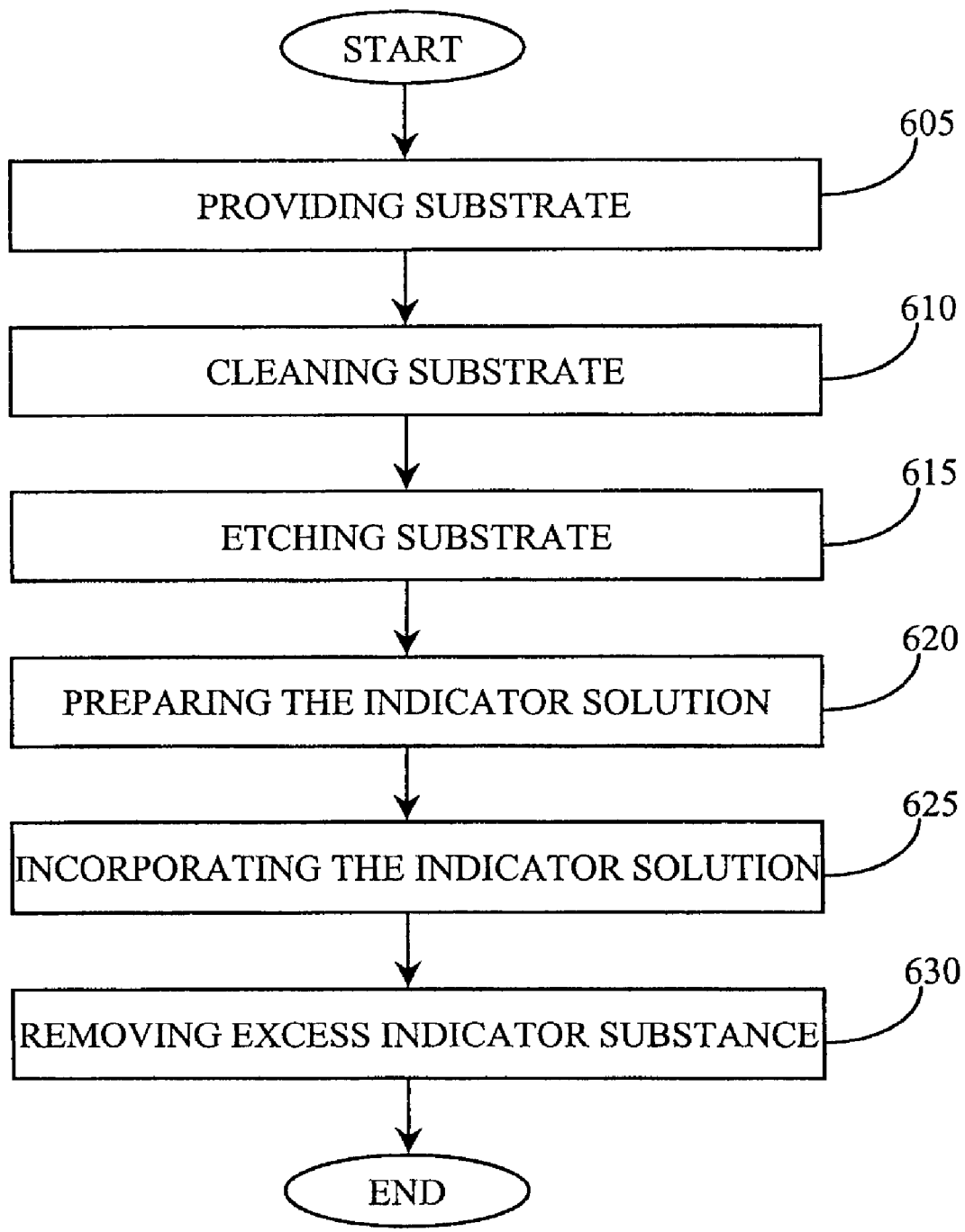
FIG. 6 is a flow chart of the method of fabricating the optrode according to one embodiment of the present invention.

Referring to FIG. 6, the process of manufacturing the optrode 204 of the present invention begins with the step of providing a substrate (box 605). The substrate is selected to be porous silica glass in the preferred embodiment, although there are a number of alternative substrate materials listed above. Moreover, the substrate may be formed by a sol-gel technique known to those skilled in the art.

The substrate selected is preferably inert with respect to the gas to be sensed and substantially transparent at a wavelength representing the color of the indicator material before or after subjected to the gas. In some embodiments, the substrate selected further includes a reversing agent, such as boron, although the reversing agent may be subsequently incorporated into the optrode by way of deposition. One example of glass having boron is sold by Corning under the Vycor® trademark.

The substrate is cleaned (box 610) prior to the subsequent etching or incorporating steps to remove any contaminants that may interfere with the deposition of the indicator material in the optrode 204. Contaminates include, for example, wax or paraffin used to secure the substrate while it is cut to size. Cleaning is accomplished by treating the substrate with a cleaning agent, such as 30 to 40 percent hydrogen peroxide solution, and heating to between 80 degrees Celsius and 100 degrees Celsius for approximately one hour while oxygen gas evolution is observed to ensure total removal of contaminants. The substrate is then immersed in deionized water, heated for one hour at approximately 80 degrees Celsius to eliminate any residual cleaning agents, and then air dried at a temperature of 100 degrees Celsius.

Alternative cleaning agents should have a polarity such that they are miscible with water in a one-to-one ratio. Suitable agents include methyl alcohol, ethyl alcohol, n-propyl alcohol, n-butyl alcohol, iso-butyl alcohol, tert-bytyl alcohol, acetonitrile, acetone, dimethyl formamide, and dimethyl sulfoxide. Detergent solutions or miscilles can also be used for cleaning the substrate.

The substrate in some embodiments is etched (box 615) subsequent to the cleaning step (box 610) to increase the surface area of the pores and ultimately the sensing surface area of the optrode 204. The etching is necessary to increase the diameter and enhance the interconnection of pores in the silica glass substrate. In the first embodiment, the mean diameter of the pores after etching is approximately 12 to 14 nanometers in cases where the sensor is intended for use with hydrogen gas. One will recognize that selection of a substrate having a pre-existing network of interconnected pores may avoid the need for etching.

Figure 7:
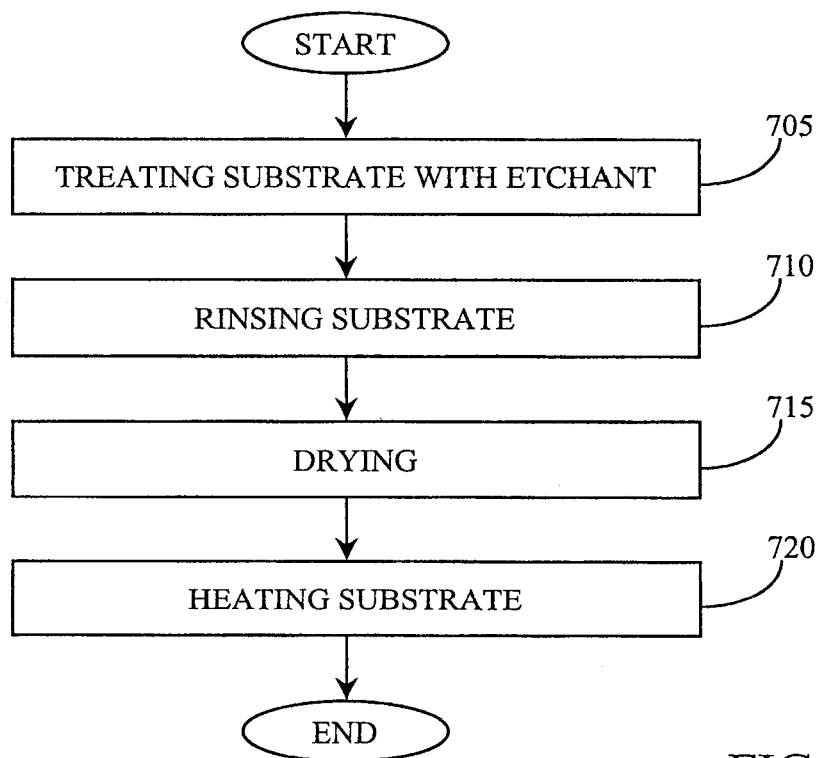
FIG. 7 is a flow chart of the method of etching the substrate.

The etching step (box 615) of FIG. 6, is illustrated in detail in FIG. 7. Etching is accomplished by treating the silica glass substrate of the first embodiment with an etchant (box 715), a 12% ammonium fluoride solution ($NH_4F$) solution at 50 degrees Celsius for 16 hours, rinsing (box 710) the substrate in deionized water, drying (box 715) at 100 degrees Celsius, and heating (box 720) to 500 degrees Celsius in air for 16 hours to drive off any residual $H_2O$ and any unwanted constituents. The substrate may then be stored in a vacuum desiccator until needed.

Other etching reagents can be utilized, either alone or in combination, including hydrogen fluoride vapor of hydrofluoric acid, cuprous chloride, ammonium chloride, silver ammonium chloride ($Ag(NH_3)_2Cl$), a solution of 23.8% hydrochloric acid, oxalic acid, and isopropyl alcohol. The concentration of etching reagent the duration of the treatment are subject to change depending on the substrate composition, the etching reagent, and the size of the substrate, for example.

When the indicator solution is applied to the substrate, the solutes are deposited in the substrate to form the indicator material. Preparation of the indicator solution (box 620) of FIG. 6 is illustrated in detail in FIG. 8. The process comprises the steps of adding a first solute to provide a reagent (box 805), an optional second solute (box 810) to provide a catalyst, an optional third solute to provide a reversing agent (box 815), and a fourth solute to provide a molecular barrier 820. In the case of the hydrogen sensor according to the first embodiment, the order in which the solutes are combined is arbitrary. However, one skilled in the art will recognize that the order in which the solutes are added or combined may become significant depending on the choice of solutes.

Figure 8:
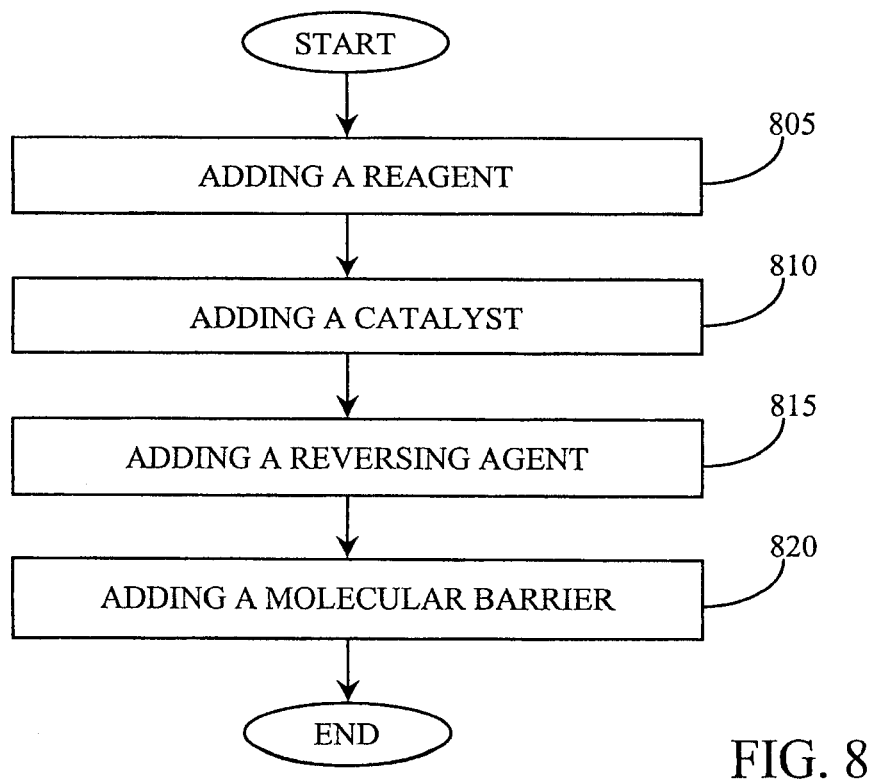
FIG. 8 is a flow chart of the method of preparing the indicator solution.

The indicator solution for sensing hydrogen gas in the first embodiment includes a water-soluble first solute, preferably a source of tungsten ion ($W^{+6}$), as shown in FIG. 8. Tungsten ion may be derived from a tungsten salt or acid including tungstosilicic acid and salts thereof, tungstophosphoric acid, organotungsten compounds, heteropolyacids of tungsten, tungsten trioxide, and ammonium tungstate. Alkali metal or alkaline earth metal salts of the tungstate ion are also appropriate as are vanadium salts or organometal complexes including vanadium oxide, vanadyl phthalocyanine, vanadium trichloride oxide, vanadium trifluoride oxide, vanadium triisopropoxy oxide, and vanadyl octaethylporphine.

Alternative reagents include sources of molybdenum ions, which may be derived from a molybdenum salt or acid including molybdosilicic acid and salts thereof, molybdenum trioxide, heteropolyacids of molybdenum, ammonium molybdate, ammonium molybdophosphate, molybdophosphoric acid, organomolybdenum compounds, and alkali metal or alkaline earth metal salts of the molybdate anion.

The preparation of the indicator solution optionally includes the step of adding a second solute (box 810), a source of a catalyst. In the preferred embodiment, the catalyst includes palladium complex ($Pd^{+2}$) in a concentration of approximately one and ten percent, preferably between one to two percent, of the tungsten ion. Suitable alternative catalysts have a neutral molecule or an ionic species with multiple oxidation states and include sources of $Pd^{+2}$, $Ru^{+3}$ or $Os^{+8}$ ions, for example.

Sources of palladium ion include palladium chloride, palladium acetate, palladium sulfate, palladium sulfite, palladium oxalate, palladium citrate, palladium pyrosulfite, palladium bromide, palladium perchlorate, palladium iodide, $CaPdCl_4$, $Na_2PdCl_4$, $K_2PdCl_4$, palladium acetylacetonate, and allylpalladium bromide. A source of ruthenium (VIII) compound includes ruthenium (VIII) oxide. A source of osmium (VIII) compound includes osmium (VIII) oxide. Other inorganic compounds with multiple stable oxidation states having redox properties compatible to reduction by hydrogen may also be used.

The preparation of the indicator solution optionally includes the step of adding a third solute (box 815), a source of reversing agent such as boron. A reversing agent returns the reagent to the state that existed prior to the introduction of gas to the sensor 201. An effective reversing agent has multiple stable oxidation states for shuttling electrons back and forth to donor and acceptor species. In the hydrogen sensor of the present embodiment, boron is used to oxidize the tungsten ($W^{+5}$ to $W^{+6}$), insuring repeatability of the hydrogen sensing process. The concentration of boron in the indicator solution should be approximately one to two percent of the reagent, preferably. The step of adding the third solute (box 815) may be avoided by selecting a substrate material that has already been doped with boron.

In addition to boron compounds, one skilled in the art will recognize the utility of a number of suitable alternative materials for reversing or reusing the reagent, including ferric (III) salts including counterions such as chloride, bromide, iodide, perchlorate, sulfate, acetate, nitrate, oxalate, acetylacetonate, and phosphate; ferric ammonium salts including chromium (VI) salts, especially the chromates or dichromates including counterions such as sodium, potassium and ammonium; cerium salts including cerium sulfate, ammonium cerium nitrate, and cerium sulfate; and other transition metal compounds (lanthanides and actinides) having multiple oxidation states with favorable redox potential for participating in electron transfer processes with the active ingredients in a manner conducive to the detection of hydrogen or target analytes in the said format.

The preparation of the indicator solution optionally includes the step of adding a fourth solute (box 820) to supply a molecular barrier. A suitable molecular barrier must be able to retain hydrogen or other gas through induced-dipole or other type of interaction. In the hydrogen sensor according to the preferred embodiment, the molecular barrier is made from calcium bromide ($CaBr_2$), although alternative substances including sodium, potassium, calcium, ammonium, lithium, beryllium, magnesium, aluminum, platinum, cobalt salts with counterions including nitrates, acetates, chloride, sulfates, phosphates, chlorates, perchlorates, nitrites, carbonates, and bicarbonates may be used.

Figure 9:
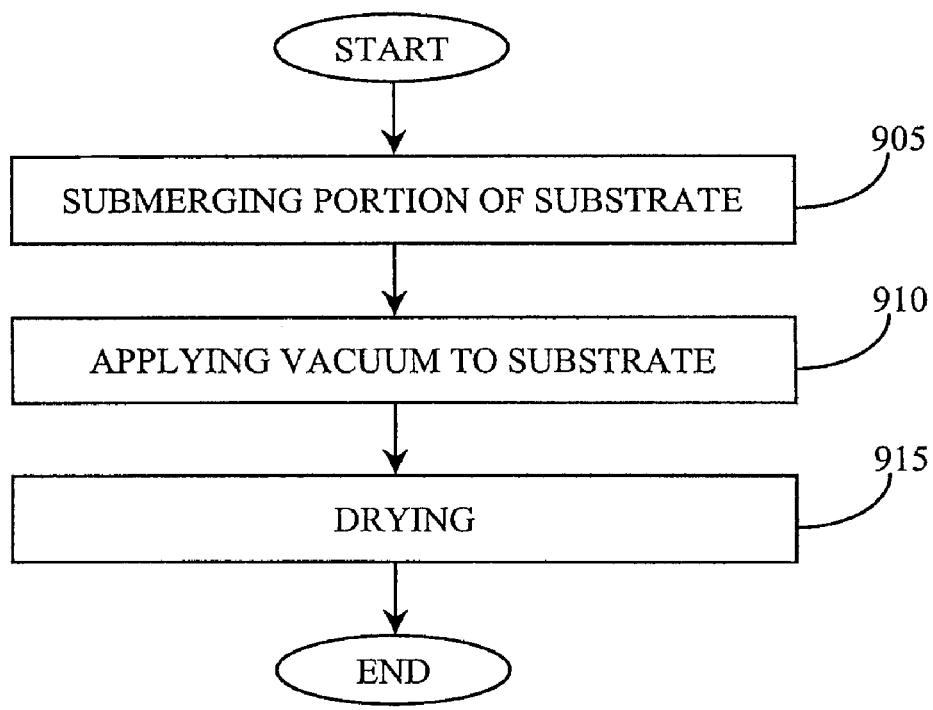
FIG. 9 is a flow chart of the method of incorporating the indicator material into the porous substrate.

The step of incorporating the indicator material (box 625), as illustrated in FIG. 6, into the substrate is illustrated in detail in FIG. 9. Using capillary action, the indicator solution is drawn into the substrate by submerging (box 905) a portion of the substrate, or otherwise placing the substrate in contact with the indicator solution, for approximately one hour. The substrate is then dried (box 915) at 100 degrees Celsius for approximately two hours, yielding the optrode 204 of the first embodiment. The "wicking" of the indicator solution allows the solution to uniformly and completely permeate the volume of the substrate without entrapping gaseous pockets in the pores. This capillary action coating process is superior to prior methods because it results in more uniform incorporation of the indicator in substantially less time.

One skilled in the art will recognize that the incorporation of indicator material by capillary action can also be achieved by soaking, evaporating, laminating, spraying, dip-coating, casting spreading, and spin-coating the indicator solution onto the substrate.

In some embodiments, the capillary action coating process further includes the step of applying (box 910) a negative pressure differential between the substrate and the indicator solution. In the preferred embodiment, a vacuum was applied to the substrate opposite the end submerged in indicator solution. The pressure differential enhances the uptake of indicator solution into the substrate and reduces the time for complete saturation of the indicator solution within the substrate.

Referring to FIG. 6 again, the substrate incorporating the indicator material is treated to remove or otherwise exfoliate loosely-bound indicator materials. In the exfoliating step (box 630) in the case of a sensor for detecting hydrogen gas, the substrate is treated with an organic solvent for a time and at a temperature sufficient to remove any palladium or tungsten species that are not tightly bound to the substrate. In the absence of the exfoliating step, the loosely-bound indicator material effectively insulates the indicator material and reduces the sensitivity of the sensor system 200.

Suitable exfoliating solvents include methyl alcohol, ethyl alcohol, n-propyl alcohol, isopropyl alcohol, n-butyl alcohol, isobutyl alcohol, tertbutyl alcohol, acetonitrile, acetone, dimethyl formamide, and dimethyl sulfoxide. A one-to-one ratio isopropyl alcohol and water solution may also be used, for example, with the glass substrate immersed for approximately one hour and dried at 100 degrees Celsius. Detergent solutions or micelles can also be utilized for the washing purpose.

Although the various features of novelty that characterize the invention have been described in terms of certain preferred embodiments, other embodiments will become apparent to those of ordinary skill in the art, in view of the disclosure herein. Accordingly, the present invention is not intended to be limited by the recitation of the preferred embodiments, but is instead intended to be defined solely by reference to the appended claims.

What we claim is:

1. A process of manufacturing an optrode for detecting a has, comprising the steps of:
    selecting a substrate that is substantially transparent to one or more input wavelengths the substrate including a plurality of interconnected pores;
    preparing the substrate to receive an indicator solution;
    producing an indicator solution that will optically change in relation to the concentration of gas comprising;
        (i) adding a source of reagent;
        (ii) adding a source of catalyst;
        (iii) adding boron; and
    incorporating the indicator solution into the pores of the substrate.

2. A process of manufacturing an optrode for detecting a gas, the method comprising the steps of:
    (a) selecting a porous substrate that is substantially transparent to visible light; the substrate including a plurality of interconnected pores;
    (b) preparing the substrate, comprising the steps of:
        (i) cleaning the substrate with hydrogen peroxide; and
        (ii) etching the substrate with ammonium fluoride solution;
    (c) producing an indicator solution, comprising the steps of:
        (i) adding a source of reagent;
        (ii) adding a source of catalyst;
        (iii) adding a boron containing reversing agent; and
        (iv) adding a molecular barrier;
    (d) incorporating the indicator solution into the pores of the substrate, comprising the steps of:
        (i) placing the substrate in contact with the indicator solution to draw the indicator solution into the pores of the substrate;
        (ii) drying the substrate; whereby indicator material is deposited into the pores of the substrate; and
    (e) removing loosely-bound indicator material with organic solvent.

* * * * *